United States Patent [19]
Chang

[11] Patent Number: 5,980,560
[45] Date of Patent: Nov. 9, 1999

[54] AIR INJECTION TYPE STOMACH BAND FOR PRESSING BACKBONE

[76] Inventor: Ikchun Chang, 694, Chayang-dong, Kwangjin-gu, Seoul, Rep. of Korea

[21] Appl. No.: 09/038,239

[22] Filed: Mar. 11, 1998

[30] Foreign Application Priority Data

Mar. 12, 1997 [KR] Rep. of Korea .......................... 97-8279
Jul. 8, 1997 [KR] Rep. of Korea ........................ 97-31600

[51] Int. Cl.⁶ ................................................... A61F 5/042
[52] U.S. Cl. .......................... 606/241; 606/201; 128/96.1; 128/99.1; 128/118.1
[58] Field of Search ..................................... 606/201, 204, 606/241; 602/13, 32, 36; 128/96.1, 99.1, 100.1, 101.1, 118.1, 112.1; 2/44

[56] References Cited

U.S. PATENT DOCUMENTS

| | | | |
|---|---|---|---|
| 4,135,503 | 1/1979 | Romano | 128/118.1 X |
| 4,682,587 | 7/1987 | Curlee | 602/13 |
| 4,682,588 | 7/1987 | Curlee | 602/13 |
| 4,703,750 | 11/1987 | Sebastian et al. | 602/13 |
| 5,450,858 | 9/1995 | Zablotsky et al. | 602/13 X |
| 5,728,055 | 3/1998 | Sebastian | 128/100.1 X |

*Primary Examiner*—Jeffrey A. Smith
*Attorney, Agent, or Firm*—Whitham, Curtis & Whitham

[57] ABSTRACT

An air injection type stomach band for distracting (e.g. stretching or extending) the lumbar vertebra of disc patients is disclosed. In the air injection type stomach band for distracting the lumbar vertebrae of disc patients, a plurality of air expansion tubes are connected perpendicularly to an air injection tube at equidistant intervals. When air is injected into the air expansion tubes, the air expansion tubes are elastically expanded so as to distract the vertebrae which constitute the lumbar vertebra. When the lumbar vertebrae are pressed, the pulpar nucleus which lies at the center of the fibrous ring is projected out. Then the projected pulpar nucleus presses the nerve, thereby causing pains in the patients. The wearing of the stomach band strengthens the fibrous ring and the lig. longitudinale anterius. Therefore, the pain is alleviated, and prevents the pulpar nucleus from being projected. Therefore, an essential treatment is possible. In this state, the wearer of this device can perform athletic exercise, so that the disc symptom can be cured. In a person who is not a disc patient, the device of the present invention protects the lumbar vertebra of the person during work or athletic exercise.

18 Claims, 9 Drawing Sheets

AIR INJECTION TYPE STOMACH BAND FOR PRESSING BACKBONE

BACKGROUND OF THE INVENTION

1. Field of the Invention

The present invention relates to an air injection type stomach and waist band for stretching or extending (sometimes referred to herein as "distracting") the lumbar vertebra of disc patients. In particular, the present invention relates to an air injection type stomach and waist pressing band for stretching or extending the lumbar vertebrae of disc patients, in which a plurality of air expansion tubes are disposed perpendicularly to an air injection tube at equidistant intervals. When air is injected into the air expansion tubes, the air expansion tubes are elastically expanded so as to distract the vertebrae which constitute the lumbar vertibrae. In this state, the wearer of this device can perform athletic exercise, so that the disc symptom can be cured. For a person who is not a disc patient, the device of the present invention protects the lumbar vertebra of the person during work or athletic exercise.

2. Description of the Prior Art

A disc patient has the following symptoms. That is, the lumbar vertibrae are composed of five vertebrae and, due to a bad posture or an excessive load, the fibrous ring which is disposed between the vertebrae is pressed. Then the pulpar nucleus which is within the fibrous ring is projected to the outside to stimulate the nerve. Consequently, the patient feels pain, and in a severe case, the waist of the patient is incapacitated.

In treating such a patient, the pressed lumbar vertebra is stretched or extended by an external force, so that the gap between the vertebrae would be restored to the original state, and that the pulpar nucleus would return to the original position. Or, alternatively, the projected pulpar nucleus is cut off, or medicine is injected into the intervertebral disc, so that the pulpar nucleus existing inside would be melted, and that the projected pulpar nucleus would be absorbed into the inside. However, with such treatment, only temporary effects are realized.

The reason is as follows. That is, the intervertebral is composed of fibrin and, therefore, the pulpar nucleus projected cannot be cured by surgery. The pulpar nucleus projected usually continuously flows out and, therefore, the symptom returns repetitively.

Therefore, an essential treatment can be realized as follows. That is, in a state with the lumbar vertibrae stretched or extended, the fibrous ring should be strengthened on a long time basis through athletic exercise. However, there has been no method or apparatus for stretching or extending the lumbar vertebra.

Recently, a stomach band made of a steel sheet has been used for correctly fixing the lumbar vertebra. However, this method makes it possible only to maintain the lumbar vertebra at the correct position, but cannot stretch or extend the lumbar vertebra. Further, with this steel band put on, an athletic exercise cannot be performed and, therefore, the fibrous ring or the lig. longitudinale anterius cannot be strengthened. Therefore, with this method, an essential treatment cannot be expected.

In an attempt to overcome the above described disadvantages of the conventional techniques, the present applicant disclosed a proposal which was filed under Korean Utility Model Application No. 94-4204. In the device of this proposal, illustrated in FIG. 12, separate connecting tubes 200 are connected to both ends of a plastic T shaped tube 100. An overlapped portion is secured by means of a connecting band 300 so as to form an air injection tube 110 of a certain length. An air expansion tube 500 vertically extends from the bottom 101 of each of the T shaped tubes 100, and the overlapped portion is secured by means of a connecting band 301. Such T shaped tubes 100 and the vertical air expansion tubes 500 are connected continuously, and this connected assembly is inserted into a securing cover 600. The securing cover 600 is provided with wrinkles 601 so that the air expansion tubes 500 can be expanded. Then the securing cover 600 is sewed to a stomach band 700.

Figure 12:
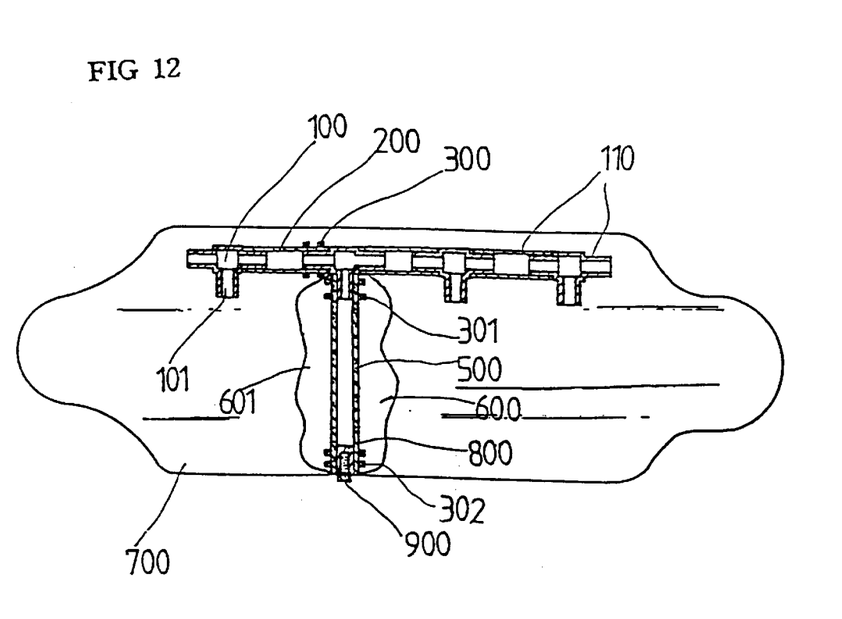
FIG. 12 is a sectional view showing the constitution of the known air injection tube.

When using the stomach band 700, in a state with the stomach band 700 attached for pressing the backbone, air is injected into the stomach band 700 through the air injection tube 110. Then the air expansion tubes 500 are expanded vertically, so as to stretch or extend the lumbar vertebra. With this stomach band put on, an athletic exercise can be performed owing to the elasticity of the air expansion tubes 500, thereby solving the conventional problems.

Figure 13:
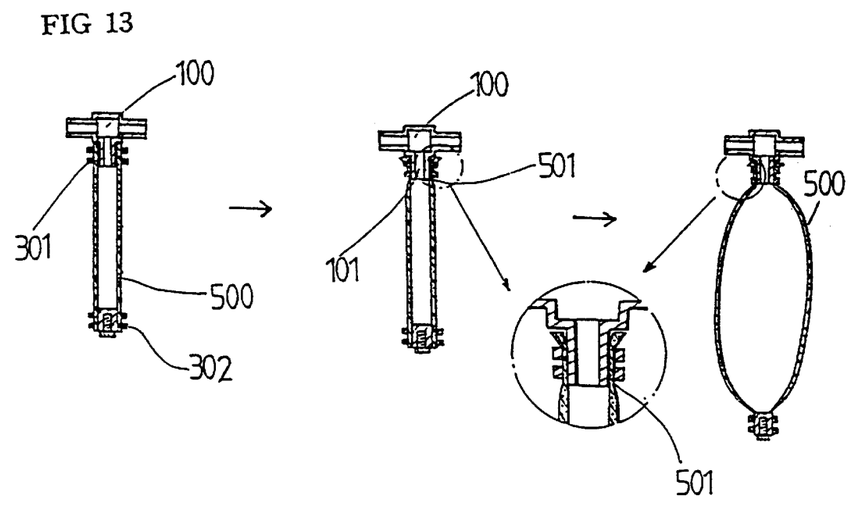
FIG. 13 is a sectional view showing an expanded state of the known air expansion tube.

In this device, however, the T shaped tubes 100 are composed of a hard material, the air expansion tubes 500 are composed of through-tubes having a certain wall thickness, and the other ends of the tubes have to be plugged with corks 800. Then the corks 800 have to be secured by means of connecting bands 302, so that the corks would not become dislodged. Further, bolts 900 are driven through the lower portions of the corks to connect them to the securing cover 600. The corks are made of a hard plastic material and, therefore, when the air expansion tubes 500 are expanded by injecting air, the corks 800 and the hard T shaped tubes 100 press the backbone. Consequently, an abrasive or chafing feeling is aggravated. Further, the air expansion tubes 500 which are connected to the T shaped tubes 100 are secured by means of connecting bands 301 in a pressed state to maintain an air-tight state. Therefore, when the air expansion tubes 500 are expanded, the pressed portions are made thin, as shown at 501, and therefore, during the use of the device, the air expansion tubes 500 are liable to rupture on the thin portion 501. Further, each of the T shaped tubes is connected to an expansion tube by using the connecting bands 300 and by using connecting tubes 200 and, therefore, numerous connecting portions exist. Therefore, much manual work must be done in manufacturing the device and the manufacturing process is complicated.

SUMMARY OF THE INVENTION

The present invention is intended to overcome the above described disadvantages of the conventional techniques.

Therefore it is an object of the present invention to provide an air injection type stomach band for stretching or extending the lumbar vertibrae of disc patients, in which separate connecting tubes are not used, T shaped tubes are made of a soft material, left and right portion of the T shaped tube are extended elongately, the left portion of the T shaped tube is contracted (has a narrow form), the right portion of the T shaped tube is expanded (has a large form) for the contracted portions to be matingly connected to the expanded portions, only the overlapped portions are made to be surrounded by connecting bands so as to form air injection tubes, the air injection tube is formed integrally or in a multi-step separated form so as to minimize the use of the connecting bands, air expansion tubes are connected vertically to the T shaped tubes, the other ends of the air expansion tubes are closed and are covered with sewed parts, an auxiliary air expansion tube is provided on the portion where the air expansion tube is connected to the T shaped tube, and the auxiliary air expansion tubes are made to be surrounded by connecting bands so that the expanded auxiliary tubes would be simultaneously expanded together with the air expansion tubes, thereby solving the conventional problems.

BRIEF DESCRIPTION OF THE DRAWINGS

The above objects and other advantages of the present invention will become more apparent by describing in detail the preferred embodiment of the present invention with reference to the attached drawings in which.

DETAILED DESCRIPTION OF THE PREFERRED EMBODIMENT

As shown in FIGS. 1 to 6, the device of the present invention is constituted as follows. That is, a T shaped connecting tube 1 includes a connecting part 4 which consists of a left contracted tube 2 and a right expanded tube 3. Thus the contracted tube 2 of one of the T shaped connecting tubes 1 is inserted into the expanded tube 3 of another of the T shaped tube 1. The overlapped portions thus formed are made to be surrounded by connecting bands 10. The contracted tubes 2 and the expanded tubes 3 thus coupled form an air injection tube 20. An air expansion tube 30 which has a closed lower end and a sewed part 31 is connected to the bottom of each of the T shaped connecting tubes 1. The overlapped portion which is formed because of the coupling between the air expansion tube 30 and the T shaped connecting tube 1 is made to be surrounded by an expansion auxiliary tube 32 reinforcement and a connecting band 11.

Figure 6:
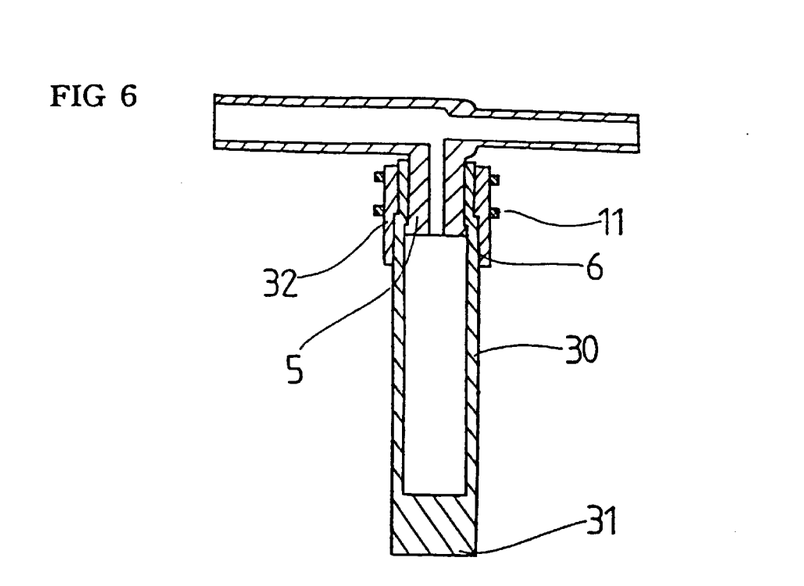
FIG. 6 is a sectional view showing the T shaped connecting tube connected to an air expansion tube.

Further, an annular projection 6 is formed on the lower end of the lower portion 5 of the T shaped connecting tube 1, so that the air expansion tube 30 would not separate from the T shaped connecting tube 1 during its expansion.

Figure 1:
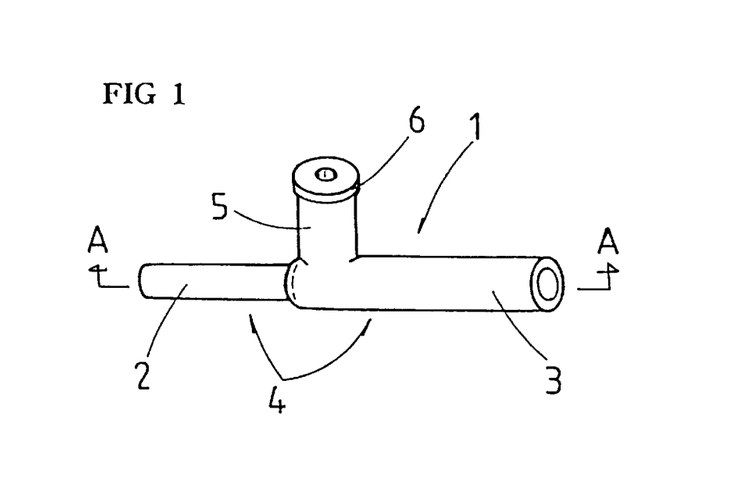
FIG. 1 is a perspective view of the T shaped connecting tube having a contracted connecting portion and an expanded connecting portion.
Figure 2:
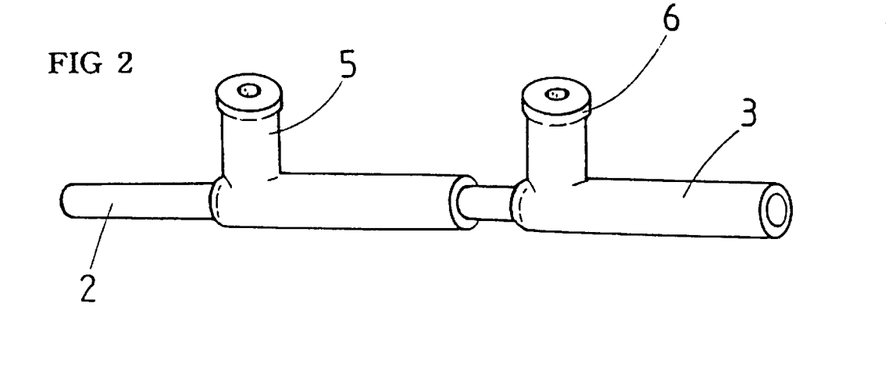
FIG. 2 is a perspective view showing the contracted connecting portion of the T shaped connecting tube connected to the expanded connecting portion of another T shaped connecting tube.
Figure 3:
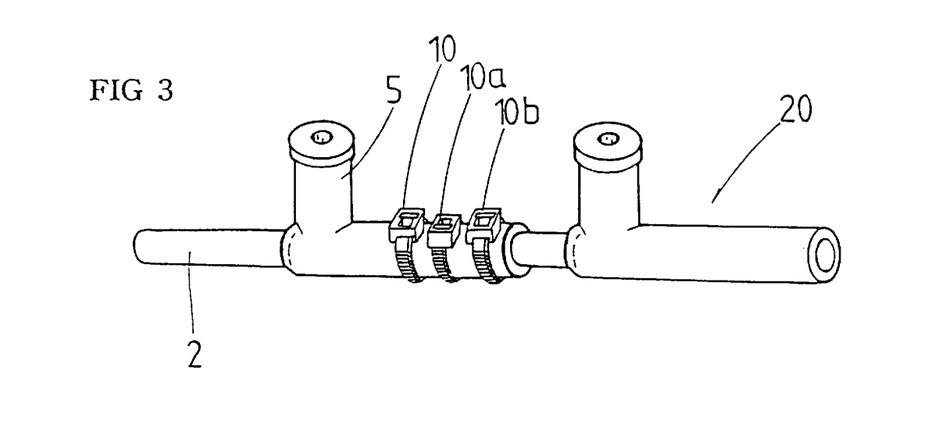
FIG. 3 is a perspective view showing a connection by means of a connecting band.
Figure 4:
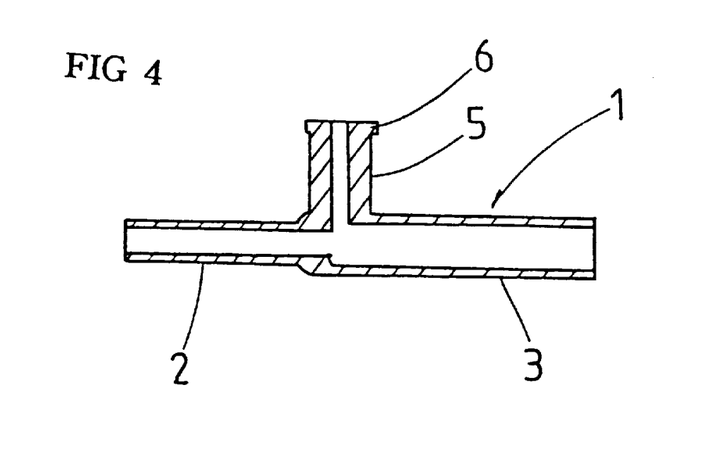
FIG. 4 is a sectional view taken along a line A—A of FIG. 1.
Figure 5:
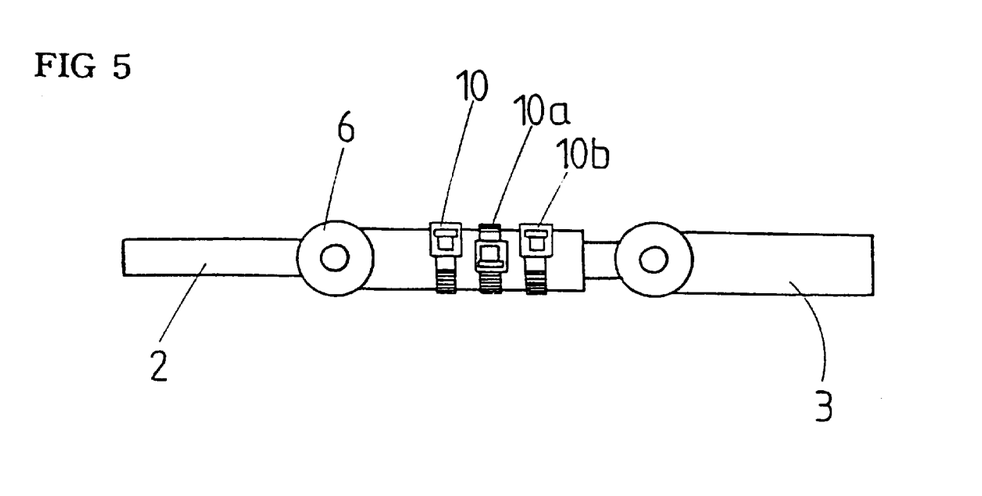
FIG. 5 is a plan view of FIG. 3.

The air injection tube 20 is made of a flexible soft material and, therefore, in order to prevent the collapsing of the tube, two or three connecting bands (10 and 11) are used, preferably disposed in a zig-zag fashion. That is, if the left and right connecting bands 10 and 10b are pressed vertically, the central connecting band 10a is horizontally pressed.

Figure 7:
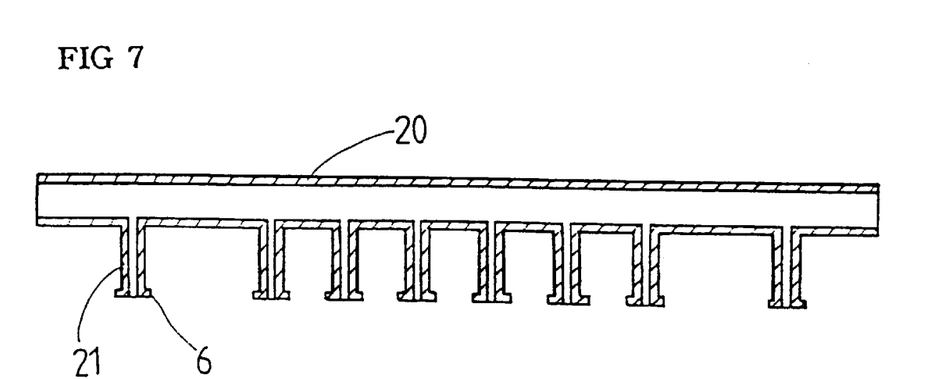
FIG. 7 is a-sectional view showing the air injection tube formed integrally.

Alternatively, in forming the air injection tube 20, the tube 20 can be formed integrally, as shown in FIG. 7, and a plurality of connecting tubes 21 each having an annular projection 6 are formed integrally thereon equidistantly.

Figure 8:
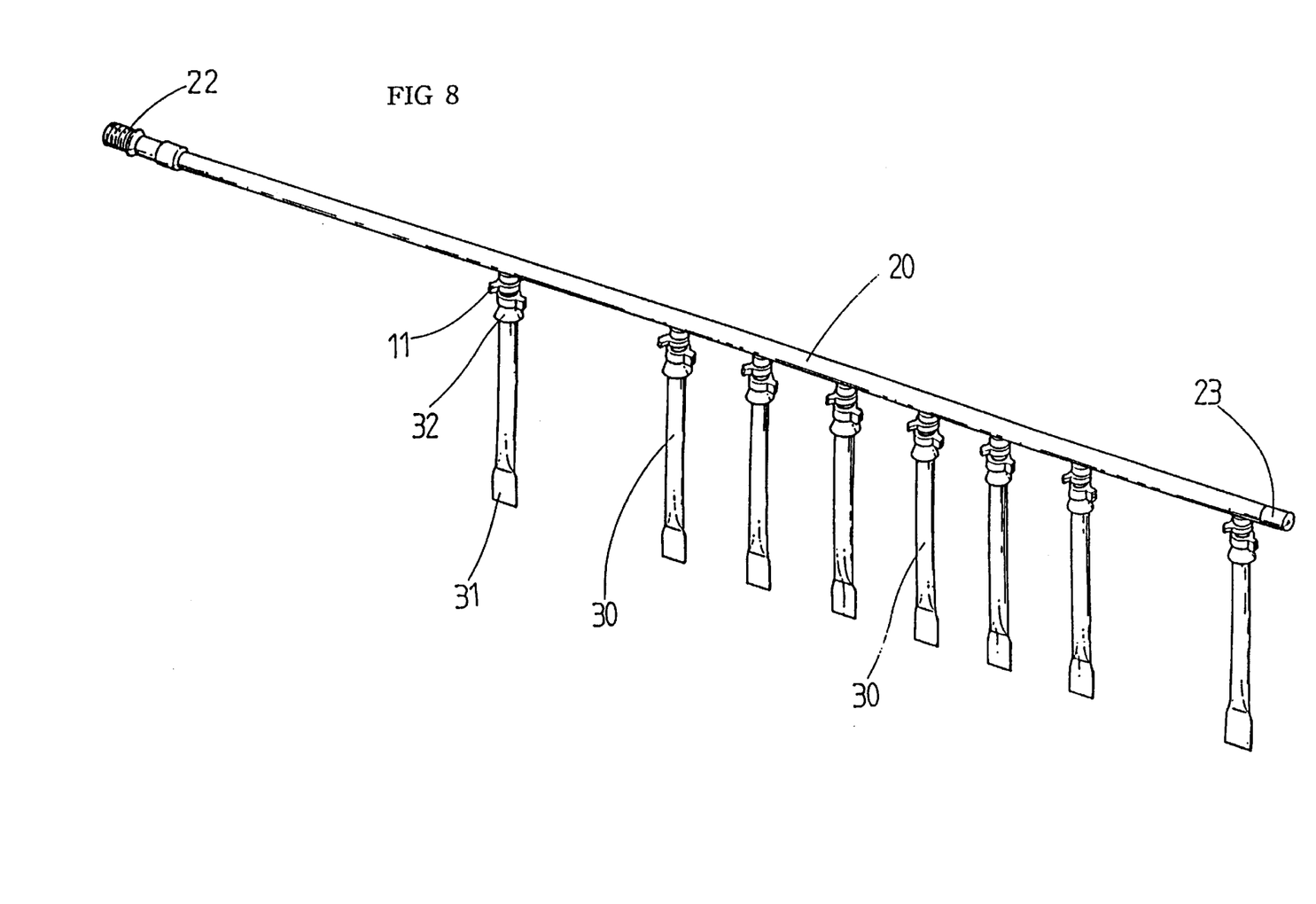
FIG. 8 is a perspective view showing an air injection tube connected to a plurality of air expansion tubes according to the present invention.

Each of the connecting tubes 21 of the air injection tube 20 is connected to an air expansion tube 30 by using a connecting band 11. Each of the air expansion tubes 30 has a closed end, and the closed end portion is secured by a sewed part 31. Further, the air expansion tube 30 is coupled with an expansion auxiliary tube 32, and in this state, the air expansion tube 30 is connected to the connecting tube 1 by means of the connecting band 11. One end of the air injection tube is open for injecting air, while the other end of the air injection tube is closed.

Figure 9:
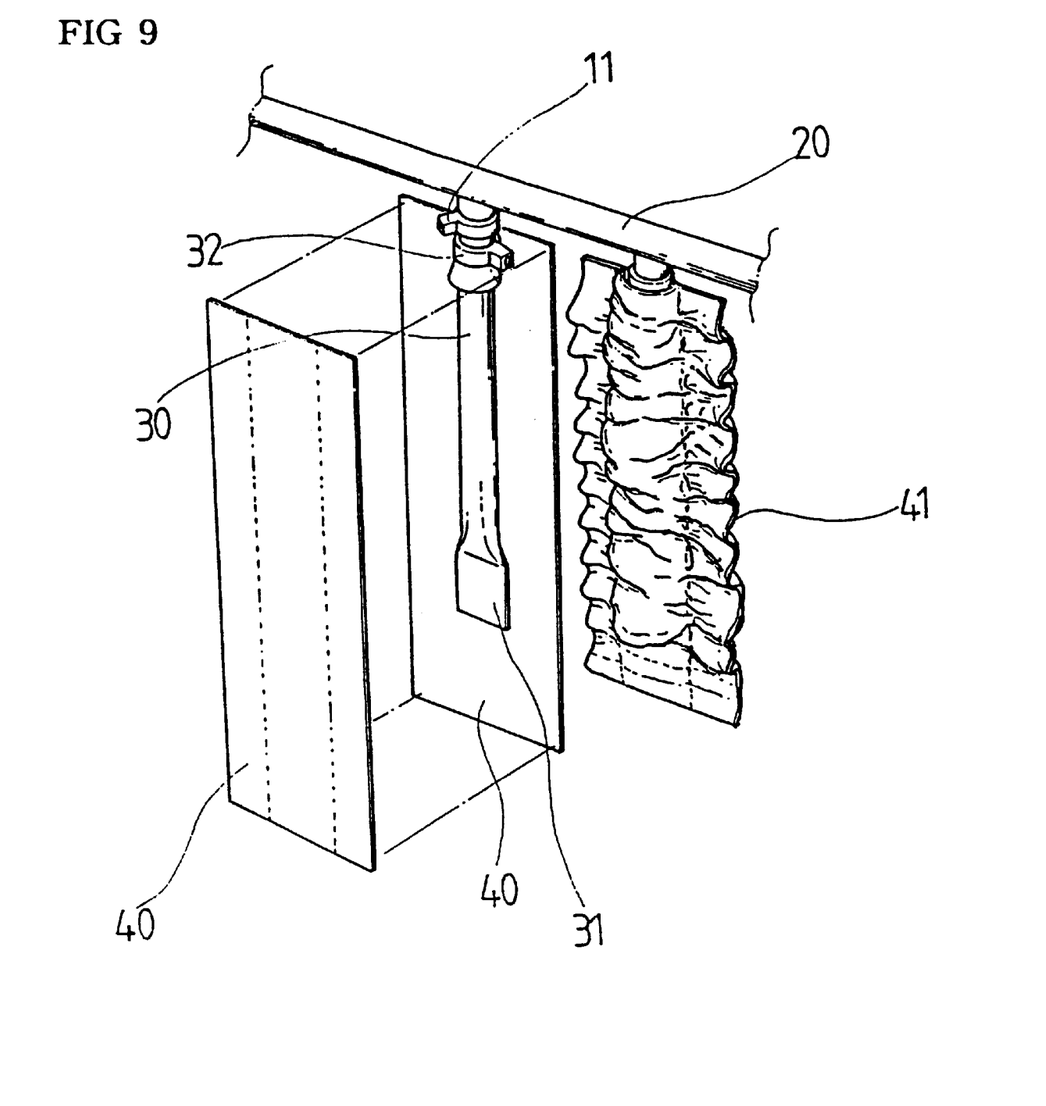
FIG. 9 is an exploded perspective view showing the coupling of the air expansion tube to the securing cover.

The air expansion tube 30 which is connected through the connecting tube 1 to the air injection tube 20 is inserted into a securing cover 40 which can accommodate the air expansion tube 30 even in an expanded state of the air expansion tube 30. In this state, the air expansion tube 30 is inserted into the wrinkled securing cover 41, shown in exploded form at 40 (FIG. 9), and is secured by the sewed part 31.

Figure 10A:
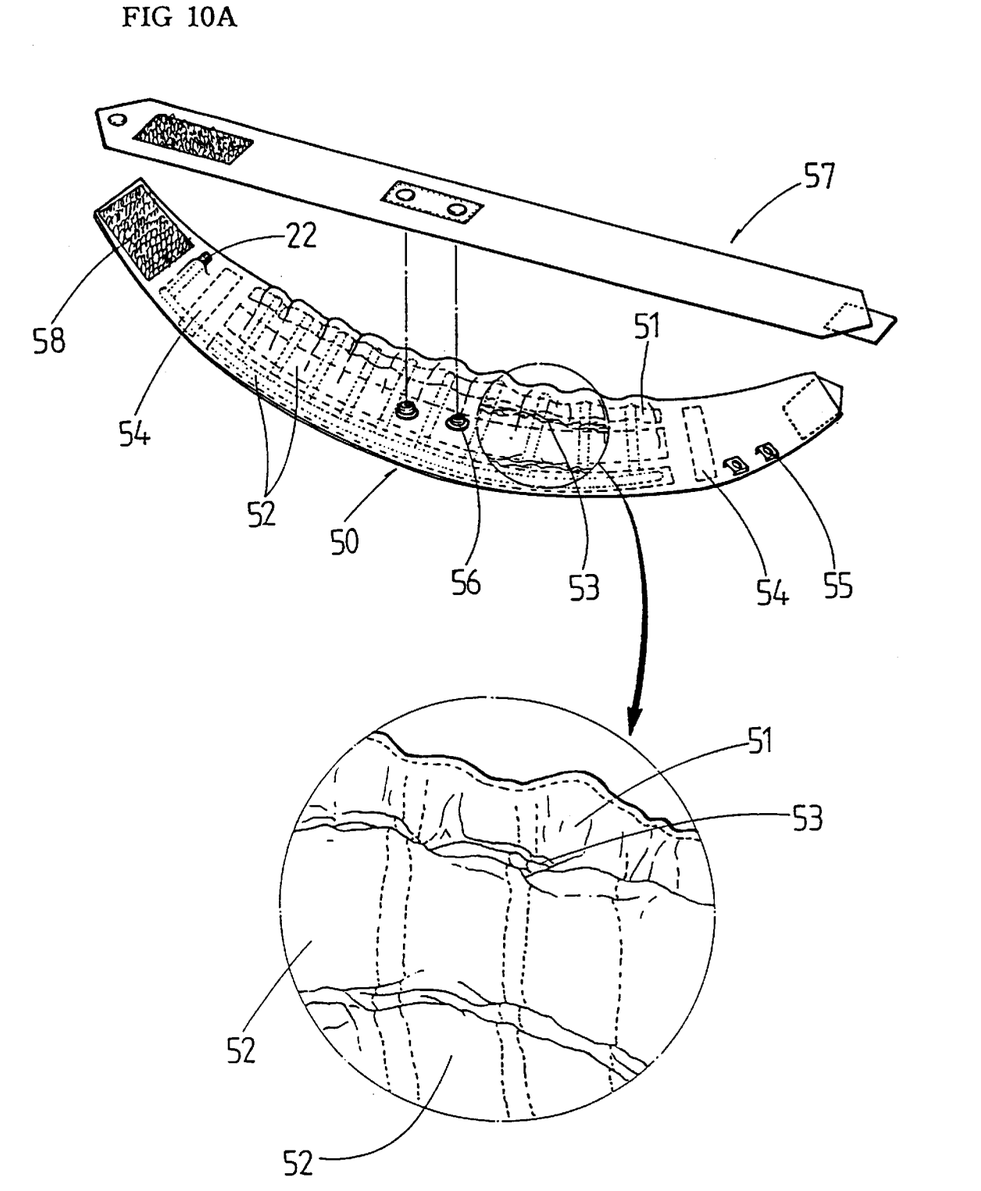
FIGS. 10A and 10B are perspective views showing the overall constitution of the device of the present invention.
Figure 10B:
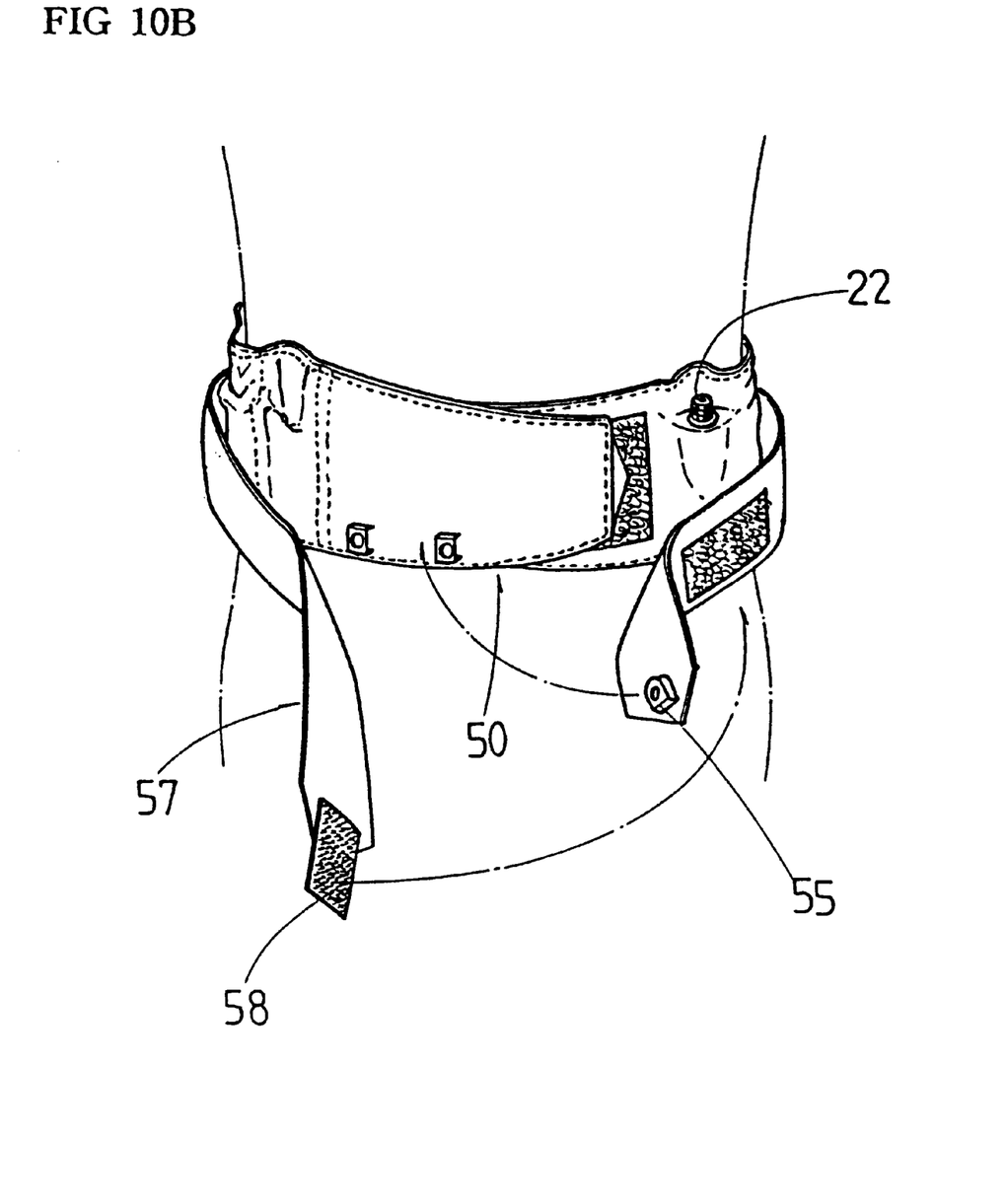

In the case where the air injection tube 20 and the air expansion tubes 30 are secured to the stomach band by sewing, an elastic band is provided along the sewed parts 31, while two reinforcing bands 51,52 are provided: one along the connecting tubes 1 and another along the middle line of the stomach band. The stomach band has wrinkles between the elastic band and the reinforcing bands. The width of the wrinkles 53 should not be smaller than the wrinkles of the securing cover 40 which has the wrinkles for accommodation of the expansion of the air expansion tubes.

Further, the stomach band is totally wrinkled, and therefore, in order to prevent distortions of the overall shape of the stomach band, there are disposed reinforcing plates 54 at the both ends of the stomach band. Thus the deformation of the stomach band is prevented, and the reinforcing plates 54 should be made of a material having a considerable strength.

Further, in the present invention, the air injection tube 20 should be made of a material which is not easily expanded under the air pressure. On the other hand, the air expansion tubes 30 should be made of a material which is easily expanded under the air pressure. Thus the air expansion tubes 30 are connected to the air injection tube 20 by means of the connecting bands 11. Alternatively, the air injection tube 20 and the air expansion tubes 30 may be made of the same material and, instead, the wall thickness of the air injection tube 20 is made thicker than those of the air expansion tubes 30, 50 that the air injection tube 20 would not be expanded under the air pressure. In this case, the air injection tube 20 can be made integrally with the air expansion tubes 30.

Further, the material of the air injection tube 20 should be flexible, so that the air injection tube 20 would not expand. Or the wall thickness of the air injection tube 20 should be thick enough to prevent expansion.

Further, if the inside diameter of the air injection tube 20 is too small, and thus if one of the air expansion tubes 30 is expanded earlier than others, then the quality of the stomach band is compromised. Therefore, the inner space of the air injection tube 20 and the inner space of the air expansion tubes 30 have to be sufficiently considered. In the preferred embodiment of the present invention, the inside diameter of the air injection tube 20 is 2 mm, while the inside diameter of the air expansion tubes 30 is 7 mm.

However, the smaller the outside diameter of the connecting tubes 1 of the air injection tube 20, the better it is, considering the connection between the connecting tubes 1 and the air expansion tubes 30. The optimum outside diameter of the connecting tubes 1 should be such that the thickness is not felt significantly.

Figure 11:
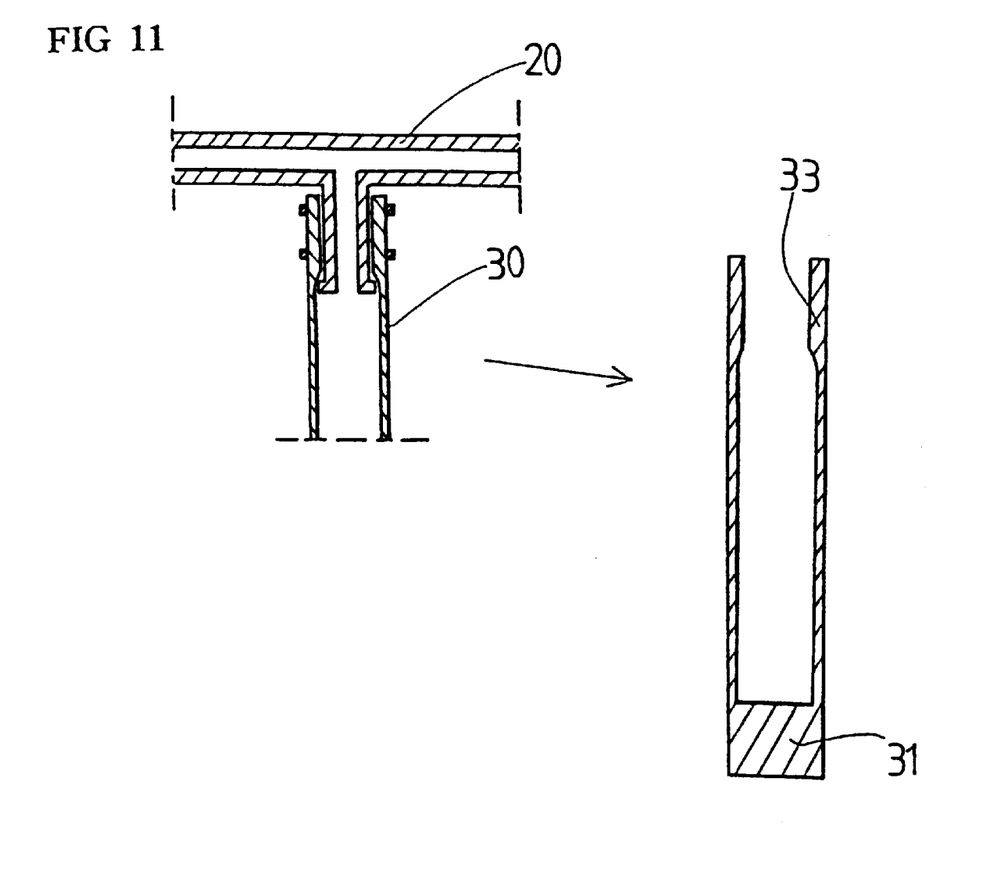
FIG. 11 is a sectional view showing reinforcing ribs formed on the air expansion tube.

As to the connecting portion where the air expansion tube 30 is connected to the connecting tube 1 of the air injection tube 20, reinforcing ribs 33 can be provided, so that the expansion auxiliary tube 32 can be eliminated.

The range of the expansion of the air expansion tubes 30 should be such that the air expansion tubes 30 would be restored to the original position upon release of the air pressure. Then the device will have an acceptable quality.

In order to make the stomach band accurately press the stomach, a VELCRO™ fastener 58 is provided on the stomach band 50, and mating buttons 56 and clips 55 are provided on the stomach band 50 and on an auxiliary band 57 to matingly couple them. One end of the auxiliary band 57 is secured by means of the mating button 56, while the other end of the auxiliary band 57 is secured by means of a VELCRO™ fastener 58, formed of mutually adhering hook and eye fabric textures.

When using the stomach band, first it is put on in such a manner as to properly press the backbone and then the auxiliary band 57 is attached to the stomach band 50. Then air is slowly pumped through an air inlet 22 which is exposed to the outside.

The air injection tube 20 and the air expansion tubes 30 are designed to withstand against an air pressure of 50 pounds per square inch. Further according to needs, the air pressure can be properly adjusted. Further, in order to realize an automatic pressure regulation, a pressure regulation valve 23 is installed on the closed end of the air injection tube 20.

Accordingly, when air is pumped in through the air injection inlet 22 into the air injection tube 20, the air expanston tubes 30 are expanded as much as the width of the securing cover in the lateral direction, while the air expansion tubes 30 are also extended in the longitudinal direction. Consequently, the lumbar vertebra which is pressed by the stomach band 50 is extended, with the result that the vertebrae constituting the lumbar vertebra are stretched or extended.

That is, owing to the air pressure which causes the air expansion tubes 30 to be extended in the lengthwise direction, the gaps between the first lumbar vertebra and the fifth lumbar vertebra are widened as much as about 3–4 mm. Therefore an increase in the lumbar vertebral anterior pulling degree was seen and the inter-segment (or inter-vertebral disc) gap between the fourth and fifth lumbar vertebrae is widened. The increase in the anterior pulling degree, the widening in the gap between the inter-vertebral discs, and the increase in the lumbar vertebral extension muscle power cause the pressure of the lumbar vertebral inter-segment discs to be decreased. Consequently, the backbone pain is alleviated and the radiating pain in the lower extremity is decreased.

As a result, the pulpar nucleus which has been projected from between the vertibrae (constituting the lumbar vertebra) is caused to be returned to the original position. Therefore, the pain is dissipated, and the inter-vertebral discs which have been damaged are healed to the normal state. Therefore, the device of the present invention cures the disc symptom in an essential manner.

In order to test the efficacy of the stomach band of the present invention, the present inventor had 22 acute and chronic backbone patients put on the stomach band of the present invention. Of them, three persons were selected in a random manner, and measured the muscle power of the lumbar vertebra by using Cybex 6000 TEF unit.

The total work amount at an angular velocity of 60 degrees per second, the peak torque, the ratio of the peak torque to the body weight, and the average power were measured. Then the measured values were analyzed by comparing the values before wearing the stomach band with the values after the wearing the stomach band. Then the values were statistically processed and the result showed that the extensor muscle power was maintained slightly longer and that the wearing of the stomach band helped reinforce the muscle power.

This test was carried out through a period of two days considering the muscle fatigue and, thus, a more exact data was obtained.

Based on the result of the test, it can be judged that the increase in the radiological lumbar vertebra anterior pulling degree comes from an increase in the muscle power besides the physical extension.

Further, owing to the wearing of the stomach band, the overall backbone movements are reduced. Regarding the effect of this feature, chronic backbone patients realized much healing effects. The healing effects were seen in 30–80% of the wearers. These effects owe to the fact that the overall bodily movements are damped and that the load on the backbone is alleviated. This means that the direct or indirect mechanical effect of the stomach band is very high.

As is emphasized in the treatment of the chronic backbone symptom, the strengthening of the lumbar vertebral extensor muscle plays an important role in healing the backbone function. Therefore, that the wearing of the stomach band strengthens the extensor muscle is confirmed in the evaluation of the uniform motion. Therefore, the efficacy of the stomach band can be acknowledged.

When evaluating the feeling of pains after putting on the air injection type stomach band on backbone patients, and when evaluating the effect of the uniform motion and when carrying out the radiological evaluation, the patients were classified into three classes: fair, poor and excellent.

In the radiological evaluation and in the uniform motion evaluation, an increase in the lumbar vertebral anterior pulling degree was seen, and a distraction or extension of 3 mm was seen in the fourth and fifth lumbar vertebral segments, while the motion of the extensor muscle was sustained longer.

Thus the effects of the stomach band of the present invention were evaluated from many different aspects, and the healing effect for acute and chronic backbone patients was almost absolute.

In the above, the stomach band according to the present invention was described as effective for the backbone symptoms. However, if the diameter of the air injection tube is properly reduced, and if the number of the air expansion tubes is properly decided, then it can be used for neck and knee.

According to the present invention as described above, distractions or extensions are caused in between the first and fifth lumbar vertebrae so as to widen the gaps between the lumbar vertebrae. Thus the projected pulpar nucleus which has been pressing the nerve is made to be restored to the original position. In this manner, the backbone pain and the disc symptom can be treated in an essential manner. Further, if the air pressures of the air expansion tubes is properly adjusted, the stomach band can be used for the general purposes such as for neck and knee. Further, the connecting bands are used in small numbers, the air tight state can be surely maintained. Further, the air expansion tubes will never explode, and the feeling to the wearer will be superior.

What is claimed is:

1. A stomach band for distracting lumbar vertebrae, comprising:

an air injection tube;

a plurality of air expansion tubes each having a closed end and an open end, the open ends being connected to a lower portion of said air injection tube by using connecting bands;

sewed parts formed at the closed ends of said air expansion tubes, for securing said air expansion tubes; and reinforcement means and connecting bands on connecting portions of said air expansion tubes.

2. The stomach band as claimed in claim 1, wherein said air injection tube is integrally formed and having a plurality of connecting tubes equidistantly spaced along said air injection tube.

3. The stomach band as claimed in claim 2, wherein as annular projection is formed at each lower end of lower portions of said air injection tube.

4. The stomach band as claimed in claim 3, wherein said connecting bands for connecting said air expansion tubes to said lower portion of said air injection tube or portion of said air injection tube, are coupled in a zig-zag form.

5. The stomach band as claimed in claim 3, further including a securing cover having wrinkles to accommodate said air expansion tube in an expanded state with said sewed part.

6. The stomach band as claimed in claim 2, wherein said air injection tube and said air expansion tubes are accommodated within a securing cover, wherein an elastic band is disposed upon said securing cover, wherein two rows of reinforcing bands are sewed under said securing cover, wherein wrinkles are formed on said securing cover between said elastic band and said reinforcing band, and said wrinkles between said elastic band and said reinforcing band have widths not smaller than wrinkles of a remainder of said securing cover to accommodate said air expansion tubes in an expanded state.

7. The stomach band as claimed in claim 2, wherein said reinforcement means includes reinforcing ribs formed on an inner circumference of an upper portion of said air expansion tube to be connected to said air injection tube.

8. The stomach band as claimed in claim 2, wherein said connecting bands for connecting said air expansion tubes to said lower portion of said air injection tube or portion of said air injection tube, are coupled in a zig-zag form.

9. The stomach band as claimed in claim 2, further including a securing cover having wrinkles to accommodate said air expansion tube even in an expanded state with said sewed part.

10. The stomach band as claimed in claim 1, wherein said air injection tube and said air expansion tube are made of a same material, but have different wall thickness, so that said air injection tube will not expand during an injection of air.

11. The stomach band as claimed in claim 1, wherein a pressure valve is installed at an end of said air injection tube.

12. The stomach band as claimed in claim 1, wherein an annular projection is formed at each lower end of lower portions of said air injection tube.

13. The stomach band as claimed in claim 1, wherein said connecting bands for connecting said air expansion tubes to said lower portion of said air injection tube or portions of said air injection tube are coupled in a zig-zag form.

14. The stomach band as claimed in claim 1, including a securing cover having wrinkles to accommodate said air expansion tube in an expanded state with said sewed part.

15. The stomach band as claimed in claim 1, wherein said air injection tube and said air expansion tubes are accommodated within a securing cover, wherein an elastic band is disposed upon said securing cover, wherein two rows of reinforcing bands are sewed under said securing cover, wherein wrinkles are formed on said securing cover between said elastic band and said reinforcing band, and said wrinkles between said elastic band and said reinforcing band have widths not smaller than wrinkles of a remainder of said securing cover to accommodate said air expansion tubes in an expanded state.

16. The stomach band as claimed in claim 1, wherein said reinforcement means includes reinforcing ribs formed on an inner circumference of an upper portion of said air expansion tube to be connected to said air injection tube.

17. The stomach band as claimed in claim 1, wherein said reinforcement means comprises expansion auxiliary tubes.

18. The stomach band as recited in claim 1 wherein said air injection tube is formed by connecting a contracted tube of one T shaped connecting tube to an expanded tube of another T shaped connecting tube.

\* \* \* \* \*